US010537767B2

(12) United States Patent  
Statham et al.

(10) Patent No.: US 10,537,767 B2  
(45) Date of Patent: Jan. 21, 2020

(54) SYSTEM AND METHOD FOR GENERATING FEEDBACK ON EXERCISE TECHNIQUE

(71) Applicant: Andrew Edward Statham, Eindhoven (NL)

(72) Inventors: Andrew Edward Statham, Eindhoven (NL); Pim Van Daelen, Eindhoven (NL); Gilad Gotman, Eindhoven (NL); Jurgen Johannes Adrianus Van Den Berg, Eindhoven (NL); Daniel Reinier Andriessen, Eindhoven (NL)

(73) Assignee: ATO-Gear Holding B.V., Eindhoven (NL)

(*) Notice: Subject to any disclaimer, the term of this patent is extended or adjusted under 35 U.S.C. 154(b) by 137 days.

(21) Appl. No.: 15/549,014

(22) PCT Filed: Feb. 5, 2016

(86) PCT No.: PCT/NL2016/050084  
§ 371 (c)(1),  
(2) Date: Aug. 4, 2017

(87) PCT Pub. No.: WO2016/126162  
PCT Pub. Date: Aug. 11, 2016

(65) Prior Publication Data  
US 2018/0028862 A1 Feb. 1, 2018

(30) Foreign Application Priority Data

Feb. 5, 2015 (NL) .................................. 2014245

(51) Int. Cl.  
*A63B 24/00* (2006.01)  
*A43B 3/00* (2006.01)  
(Continued)

(52) U.S. Cl.  
CPC ........ *A63B 24/0006* (2013.01); *A43B 3/0005* (2013.01); *A43B 17/00* (2013.01);  
(Continued)

(58) Field of Classification Search  
CPC ...................................................... A63B 24/00  
See application file for complete search history.

(56) References Cited

U.S. PATENT DOCUMENTS

2012/0015778 A1* 1/2012 Lee ..................... A63B 71/0622  
482/8  
2014/0195023 A1* 7/2014 Statham ............... A61B 5/1038  
700/91

FOREIGN PATENT DOCUMENTS

EP 2260910 A1 12/2010  
EP 2407219 A2 1/2012  
(Continued)

OTHER PUBLICATIONS

International Search Report PCT/NL2016/050084 dated Jul. 25, 2016.

*Primary Examiner* — Omkar A Deodhar  
(74) *Attorney, Agent, or Firm* — Pillsbury Winthrop Shaw Pittman, LLP

(57) ABSTRACT

A system and method for generating feedback on exercise technique. The system comprises a sensor and readout device to generate sensor data based on the exercise technique, e.g. pressure signal exerted by a foot. A data processor processes the sensor data to calculate a feedback value. A color mapper maps the feedback value onto a color map to transform the feedback value into a color value. A wearable feedback device comprising a light source generates a variable color light output based on the color value. For example, a mode selector provides selection between a plurality of feedback modes, wherein the selection of a (Continued)

feedback mode result in selection of a feedback algorithm for the data processor and selection of a color map for the color mapper.

14 Claims, 9 Drawing Sheets

(51) Int. Cl.
- *A43B 17/00* (2006.01)
- *A63B 69/00* (2006.01)
- *A63B 71/06* (2006.01)
- *G09B 5/02* (2006.01)
- *G09B 19/00* (2006.01)

(52) U.S. Cl.
CPC ...... *A63B 24/0062* (2013.01); *A63B 69/0028* (2013.01); *A63B 71/0622* (2013.01); *G09B 5/02* (2013.01); *G09B 19/0038* (2013.01); *A63B 2071/0663* (2013.01); *A63B 2220/12* (2013.01); *A63B 2220/20* (2013.01); *A63B 2220/30* (2013.01); *A63B 2220/62* (2013.01)

(56) References Cited

FOREIGN PATENT DOCUMENTS

| EP | 2556795 A1 | 2/2013 |
|----|-----------|--------|
| GB | 2476458 A | 6/2011 |

\* cited by examiner

SYSTEM AND METHOD FOR GENERATING FEEDBACK ON EXERCISE TECHNIQUE

CROSS-REFERENCE TO RELATED APPLICATIONS

This is the U.S. National Stage of PCT/NL2016/050084, filed Feb. 5, 2016, which in turn claims priority to Netherlands Application No. 2014245, filed Feb. 5, 2015, the contents of both applications being incorporated herein by reference in their entireties.

TECHNICAL FIELD AND BACKGROUND

The present disclosure relates to a system and method for generating feedback on exercise technique, e.g. running style.

For example, WO 2013/022344 describes a system and method for providing feedback to a user on the reactivity of his running style. A pressure sensitive surface records a gait line of the center of pressure exerted by the user's foot on an underlying surface during a footstep period. The reactivity describes the viscoelastic behavior of the muscle-tendon unit and is calculated as a function of the loading time and/or the distance moved by the center of pressure backwards towards the heel. Correspondingly, feedback is provided to the user about his running reactivity. The feedback may be one or more of a visual, audio, or haptic feedback signal. For example, a human interface may comprise a display providing a visual feedback signal to the user as a function of the calculated reactivity. The display may e.g. simply display a number that is proportional to the calculated reactivity and/or display a graph, e.g. a bar graph that extends as a function of the reactivity. The display could also provide a feedback by varying the color of a displayed image as a function of the calculated reactivity.

For example EP 2 407 219 A2 describes a portable fitness monitoring device which may include a visual display output device, e.g. a wrist band having one or more visual displays such as devices disclosed in EP 2 260 910 A1. While the known visual display output device is suitable to give feedback on some physiological parameters such as heartbeat, it is found less suitable to provide feedback on exercise technique, in particular for biomechanical parameters which can change each foot step. For example, when the user is forced to change and hold the posture of his arm to view the known visual display output device, this will inevitably affect his walking technique.

There is yet a desire to provide intuitive and easy to customize feedback on different aspects of a person's exercise technique while minimally disturbing the exercise technique.

SUMMARY

A first aspect of the present disclosure provides a system for generating feedback on exercise technique. The system comprises a sensor configured to generate a sensor signal as a function of one or more aspects of the exercise technique, e.g. biomechanical aspects such as measured from pressure, angle, acceleration, speed, etcetera, of one or more body parts. The system comprises a readout device configured to generate sensor data based on the sensor signal. The system comprises a data processor configured to process the sensor data to calculate a feedback value; a color mapper configured to map the feedback value onto a color map to transform the feedback value into a color value. The system comprises a wearable feedback device comprising a light source configured to generate a variable color light output based on the color value.

Preferably, the system comprises a mode selector configured to provide selection between a plurality of feedback modes. The selection of a feedback mode results in selection of a feedback algorithm for the data processor and selection of a color map for the color mapper. The selected feedback algorithm and color map are uniquely specific for each feedback mode. Based on the selected feedback mode, the data processor is configured to process the sensor data according to the mode-specific feedback algorithm to calculate the feedback value according to the selected feedback mode. The color mapper is configured to map the calculated feedback value onto the mode-specific color map for transforming the feedback value into the color value according to the selected feedback mode.

To improve exercise technique, e.g. running style, it is presently recognized a user needs intuitive real-time feedback that can enable him to correct his technique while performing the exercise and without interference. This means that the feedback should be easy to interpret. However, an exercise technique such as running style has many different aspects that can be quantified in various ways. Conventional portable feedback systems may use audio feedback that can restrict the users ability to hear and/or prohibit or interrupt the users ability to listen to music or receive other instructions from, for example, a coach.

Other feedback systems may utilize a screen that limits portability and is not possible to easily view whilst exercising outdoors without disturbing the technique since the user must restrict movement of his arms to view the screen, or require the user to wear glasses which are not always practical or possible for the user to wear. With the present solution it is possible to process the information collected from the user in an automated fashion so that it can be translated or encoded into a colour scale. The user is informed (or determines themselves) about how to interpret this scale prior to their run. Reducing complex parameters to a visual color scale allows the user to receive real time continuous feedback whilst exercising without interfering with the said activity and without inhibiting the user's ability to see, hear or move freely.

By providing a user input device configured to provide user selection between the plurality of feedback modes, the user can easily choose a particular aspect of his exercise technique or style. Since feedback is provided only for one aspect of the technique at a time, the user can concentrate on improving that aspect using the intuitive color feedback of his wearable device. For example, a touch sensitive display, e.g. mobile phone app, can be configured to display a menu of different feedback modes and change the feedback mode following touch selection of an item in the menu. The selection of the mode can be communicated with the readout device and/or feedback device to change the algorithm and/or color map.

By converting the feedback value to a single number, it can be easily mapped onto a one dimensional color scale that is easy to interpret. For example, a color scale can define color values over a range of expected feedback values. For example a color value of the color map can be defined as a function of feedback value wherein the color map comprises color values defining a hue of light output from the light source. By using a color scale with contrasting colors on different ends of the value range, the user can get clear feedback about the aspect of his running style, in particular, where on the scale he is currently operating. By using a color map with a gradient color scale, the user can intuitively interpret where he relatively operates on the color scale e.g. between two colors. By providing at least three distinct colors on the color scale, a user can also get feedback if he currently operates in the middle of two extreme feedback regimes, i.e. a neutral style. Intuitively, a white color of the light can be provided in the middle of the color scale which is naturally interpreted as a neutral value for the current aspect of the running style. By providing a white light in the middle of the scale instead of e.g. no light, a user can positively verify that the feedback device is still active. Besides hue, the color values may also define a brightness of light output from the light source. For example the color values can be encoded as RGB values A position on the color map is associated with a feedback value calculated by the data processor and the color value on the color map is associated with a color output of the light source. The light source may comprise one or more light emitting devices. Each of the devices may emit the feedback color or the combined light of the devices may provide a user impression of the feedback color. For example if a red, green, and blue light emitting device are combined, they can be combined with relative brightness to provide a feedback color based on an RGB value. Accordingly, one or more light sources on the feedback device can provide a single combined color impression corresponding to the color value selected from the color map based on the feedback value.

By providing user customization of the color map, the colors can be adjusted to personal preference, style, or physique. Some parameters may e.g. depend on a weight, size or age of the user. By providing adjustment of the color value, a user can customize the color he associates with values of the feedback scale. By providing adjustment of the position or threshold where colors are on the feedback scale, a user can customize different feedback regimes. By providing the mode selection and color selection in a single device, e.g. mobile phone, the user does not have to switch devices to easily select and customize an aspect of his style or technique.

By providing a user interface depicting a color map representation over a range of feedback values, a user can easily select and interpret the color scale. By providing a slider control a position of colors on the color map representation can be easily adjusted. For example, the displaceable soft button or other feature can be shown on a touch sensitive display. By displaying a location of one or more feedback values on a respective color map representation (e.g. of a previous or current exercise), a user can evaluate his current style or technique and adjust color values and/or positions accordingly in an intuitive way.

It is found that many relevant feedback values can be derived from a pressure sensitive surface, e.g. placed in the shoe. Advantageously, a pressure sensitive insole is a relatively simple device that can be placed in any existing shoe. The pressure sensitive surface typically comprises a plurality of pressure sensors to generate a pressure signal indicative of a pressure distribution exerted on the pressure sensitive surface. In this way, various complex parameters and can be derived e.g. from a gait line or pressure center. By shaping the pressure sensitive surface as an insole, the sensor can be easily used in an existing shoe. The pressure surface may have an integrated or separate readout device. By attaching the readout device to the shoe, it can be avoided that wires have to run from the shoe to other parts of the body. By providing the readout device with a wireless transmitter, readout data can be transmitted to other devices. For example two or more devices can transmit and/or receive wireless data from each other. For example a standard interface such as bluetooth can be used to interface also with existing devices such as a mobile phone.

By recording a time-dependent measurement of the pressure signal, more complex feedback values, e.g. related to the movement of a foot during a step, can be derived. For example, the feedback value can be calculated from a pressure gait line formed by a moving center of pressure on the pressure sensitive surface. By using pressure sensitive insoles in both shoes, further feedback parameters can be derived, e.g. based on a comparison between the feet. By combination of time dependent measurement and two insoles, e.g. balance or time of flight between steps can be derived. Also further sensors and devices can be used in combination with the insole to derive further parameters. For example, using a GPS device can allow measurement of speed, which can be combined with step frequency to derive stride length. The speed can also be derived from the pressure surface itself. Each of the feedback values can be interesting for a user to change or maintain his running style. Accordingly, for each feedback mode a complex measurement can be converted to a location on a color map to provide intuitive feedback. By calculation of a pressure coordinate of a location on the pressure sensitive surface and mapping the pressure coordinate onto a corresponding map coordinate of a location on the color map a color value can be determined in an intuitive way. For example a center of pressure can be determined to provide feedback on strike index location. For example, a feedback value is mapped on a color value by a table lookup and/or interpolation of color values defined at specific feedback values.

By representing the color map as a surface profile picture of the pressure sensitive surface, e.g. shoe/insole profile, positions in the surface profile picture can be directly linked to positions on the pressure sensitive surface. If a feedback value comprises a location on the pressure sensitive surface, the location can be mapped onto a corresponding coordinate of the surface profile picture for determining the color value. For example, the feedback value comprises a coordinate of a center of pressure on the pressure sensitive surface which can be mapped onto a corresponding coordinate of the surface profile picture for determining the color value indicative of a strike index location, i.e. where a user lands on his foot. Advantageously, providing feedback on a linear color scale along a length of the foot can be relatively easy to interpret, and the user can adjust e.g. the way in which he lands his foot to reach a desired running style.

A second aspect of the present disclosure provides a method for providing feedback on exercise technique such as running style. The method comprises selecting a feedback mode with a mode-specific feedback algorithm and color map. The method further comprises receiving sensor data corresponding one or more aspects of the exercise technique, e.g. pressure exerted on a pressure sensitive surface or acceleration of a sensor during running. The method comprises processing the sensor data according to the mode-specific feedback algorithm to calculate a feedback value. The method further comprises mapping the feedback value onto the mode-specific color map to transform the feedback value into a color value and controlling a light source to generate variable color light output based on the color value. By selecting the feedback mode from a plurality of feedback modes, each feedback mode can be distinguished by a mode-specific feedback algorithm and color map. By providing a user selectable feedback mode the user can train various aspects of his running style. Methods as described herein can be partially or fully executed by one or more computers, i.e. computing devices. For example, a method can be embodied as a computer readable medium with program instructions, wherein the program instructions, when executed on one or more computers, cause the one or more computers to execute one or more methods as described herein.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1:
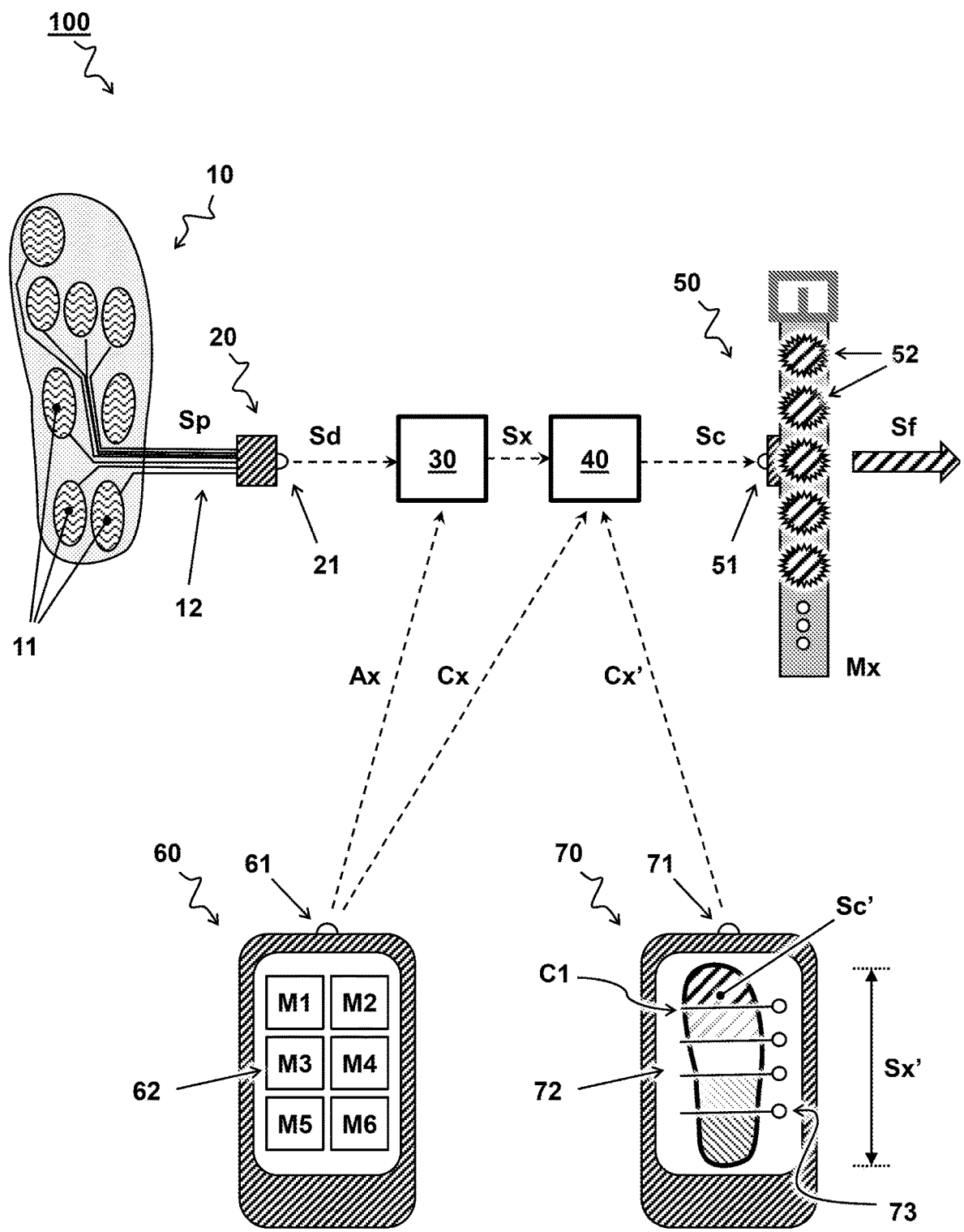
FIG. 1 illustrates an embodiment of a system for generating feedback on running style.

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise. All publications, patent applications, patents, and other references mentioned herein are incorporated by reference in their entirety. In case of conflict, the present specification, including definitions, will control.

In one embodiment, the system translates data from biomechanical sensors into real time continuous feedback on exercise technique, biomechanics, e.g. running or walking style via a light emitting feedback device worn on the body. For example, a system and method for providing feedback to a user on his or her exercise technique via a wrist unit. The system employs e.g. a pressure sensitive surface to measure the pressure distribution in time and resolve a number of biomechanical parameters e.g. center of pressure, record a gait line of the center of pressure exerted by the user's foot on an underlying surface during a footstep period, balance of contact time, flight time and pressure between the left and right feet.

The resulting data from the pressure measurements may or may not be pre-processed and subsequently wirelessly transmitted to a receiving unit that may be a mobile phone, computer or other processing unit. The resulting parameters can be translated into a point on a representative scale and transposed onto a color map. The corresponding color and scale point data is transmitted to a receiving feedback unit that can be worn on the body, most commonly on the arm, hand or wrist.

Feedback is provided to the user via a light emitting device worn on the body during exercise. The feedback unit converts the point data into the corresponding color and light intensity that is emitted by light emitting components (e.g. LED) that can be viewed by the user during exercise. Especially the intensity and position of the light emitting feedback unit will enable the exercising user to be able to receive feedback in their peripheral vision even whilst looking ahead, enabling the user to better perceive direction, obstacles and potential hazards, whilst maintaining a proper running form.

The colour and intensity of the light emitted thus correlates to the data collected by sensors detecting how the user is moving. This correlation is determined by an algorithm providing a result corresponding to a colour map and rating scale, the ranges of the scale and the colour map may optionally be adjusted by the user. The user selects the parameter or technique aspect on which they will focus for their subsequent exercise and is informed on how to interpret the output scale. In this way the user can look ahead whilst exercising, and listen to music, be aware of hazards, hear instructions etc. whilst simultaneously receiving feedback in their peripheral vision regarding the way they are running.

In one embodiment changes can additionally be alerted to the user via vibrating actuators that will make the feedback unit vibrate and alert the user to changes that can be viewed via the emitted light. Alternatively, or in addition, in one embodiment an intensity of the light is modulated, e.g. blinking, to indicate passing of a threshold, e.g. from one range into another range. It will be appreciated that a blinking light can be particularly perceptible in a peripheral part of the vision.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1 shows a system 100 for generating feedback on running style.

In one embodiment, the system comprises a pressure sensitive surface 10 configured to generate a pressure signal Sp as a function of pressure exerted on the pressure sensitive surface 10 during running. For example, the pressure sensitive surface 10 comprises a plurality of pressure sensors configured to generate a pressure signal Sp indicative of a pressure distribution exerted on the pressure sensitive surface 10. For example, the pressure sensitive surface 10 is shaped as an insole for placement inside a shoe. It is presently recognized that the sensor data Sp from a pressure sensitive surface in the shoe can provide accurate measurement of many different aspects of a person's running or walking style. Whilst such measurement is conventionally difficult to interpret for a user, especially during the exercise, the present systems and methods can translate the complex sensor data into an intuitive feedback mechanism.

It will be appreciated that the systems and methods for translating complex sensor data into intuitive feedback can also be applied to other sensors or combinations of sensors than a pressure sensitive surface. For example another type of (bio)mechanical sensor or combination of sensors can be used to measure one or more aspects of an exercise technique. Exercises may include e.g. running, walking, hiking, jumping, climbing, rehabilitation, etcetera. Aspects of an exercise for which feedback can be provided may include e.g. pressure on a walking surface, angle of one or more joints, angle of placing the foot, contact time of the foot, balance between the feet, air time between feet touching the ground, pronation, heel lifting speed, etcetera. For example an accelerometer, e.g. attached to the shoe or another part of the body, can be used instead of, or in addition to, a pressure sensitive surface to measure one or more aspects of an exercise technique such as the impact velocity of a foot on the ground. For example, an angle sensor can be configured to measure an angle of a joint, e.g. knee to derive additional or alternative sensor data to measure aspects of the exercise technique.

In one embodiment, the system comprises a readout device 20 configured to generate sensor data Sd based on the sensor signal Sp of the sensor 10, e.g. pressure sensitive surface. In one embodiment, the readout device 20 comprises attachment means for attaching the readout device 20 to a shoe. In one embodiment, the readout device 20 comprises a wireless transmitter 21. The readout device 20 can be integrated or separate from the sensor, e.g. pressure sensitive surface 10

In one embodiment, the system comprises a data processor 30 configured to process the sensor data Sd to calculate a feedback value Sx. This and other processors may comprise dedicated components or be integrated, e.g. part of a general purpose CPU. The processor may include microprocessors, central processing units (CPUs), digital signal processors (DSPs), ASICs, or any other processor(s) or controller(s) such as digital optical devices, or analog electrical circuits that perform the same functions, and employ electronic techniques and architecture. The processor is typically under software control for example, and has or communicates with a memory that stores the software and other data such as user preferences, parameters, evaluation ranges, and/or time, bandwidth, and fraction thresholds.

In one embodiment, the system comprises a color mapper 40 configured to map the feedback value Sx onto a color map Cx to transform the feedback value into a color value Sc. The color value may determine the color of light in a feedback device. In one embodiment, the system comprises a feedback device 50 comprising a light source 52 configured to generate a variable color light output Sf based on the color value Sc. Preferably, though not necessarily, the feedback device 50 is wearable, e.g. has attachment means for carrying the device on the body. For example, the feedback device 50 comprises a wrist or arm band (or glove or cuff on the lower arm). The device may also be attached by other means, e.g. clasps, buttons, velcro, etcetera. In one embodiment, the feedback device 50 comprises a wrist band with one or more light sources 52 and a wireless receiver 51 to receive the color value Sc. The data processor 30 and color mapper 40 may also be integrated in the wrist band device, wherein the device directly receives the sensor data Sd. For example, the feedback algorithm Ax and color map Cx can be uploaded to the wearable device from the mode selector 60 and/or color map selector 70, e.g. a mobile phone. Advantageously, the mobile phone need not be carried around whilst exercising. A mode selector 60 can also be integrated e.g. in a wrist band, for example a button of slide to select between different feedback modes.

In one embodiment, an intensity and position of one or more light sources is configured to enable an exercising user to be able to receive visual feedback predominantly in their peripheral vision even whilst looking ahead, i.e. not directly looking at the light source. This may enable the user to better perceive their surrounding whilst maintaining a proper running form, e.g. swinging the arms at the side of the body. For example, as shown in the figure, the wrist band comprises a plurality of light sources 52, wherein the light sources are in use arranged around a circumference of the user's wrist, i.e. when the wrist band is worn by the user. Advantageously, the light source may thus be positioned on all sides of the wrist and can be easily viewed in a peripheral vision of the user during exercise. For example one or more light sources are arranged so that when the arm of a user comes forward during running, the light source projects into the peripheral vision of the user but does not require the user to take their view away from the terrain or obstacles if they are running. This is in contrast e.g. to a regular display disposed only on one side of a wrist band which is not visible from all directions of the wrist and typically not visible without changing posture of the arm which may affect the posture and exercise technique. Furthermore, an intensity of a normal display is configured to be visible when directly viewed but may not allow distinguishing a color when only viewed in a peripheral part of the vision. Accordingly, the light sources as used herein are preferably relatively bright compared to surrounding light.

In one embodiment, the system comprises a mode selector 60 configured to provide selection between a plurality of (visual) feedback modes M1,M2. For example, the selection of a feedback mode results in selection of a feedback algorithm Ax for the data processor 30 and selection of a color map Cx for the color mapper 40. Preferably the selected feedback algorithm Ax and color map Cx are uniquely specific for each feedback mode Based on the selected feedback mode, the data processor 30 is configured to process the sensor data Sd according to the mode-specific feedback algorithm Ax to calculate the feedback value Sx according to the selected feedback mode and the color mapper 40 is configured to map the calculated feedback value Sx onto the mode-specific color map Cx for transforming the feedback value Sx into the color value Sc according to the selected feedback mode.

In one embodiment, the mode selector 60 comprises a user input device configured to provide user selection between the plurality of feedback modes M1,M2, etc. In one embodiment, the user input device 60 comprises a touch sensitive display 62 or user interface configured to display a menu of different feedback modes M1,M2 and change the feedback mode following touch selection of an item in the menu. In one embodiment, the user input device 60 comprises a wireless transceiver 61 for communicating with the readout device 20 and/or feedback device 50, e.g. via respective transceivers 21 and/or 51.

In one embodiment, the system comprises a color map selector 70 configured to provide user customization of the mode-specific color map Cx, wherein the customization comprises adjustment of color values and/or positions on the color map. In one embodiment, the color map selector 70 comprises a user interface 72 depicting a color map representation C1, wherein the representation C1 comprises a color scale displaying color values Sc' over a range of feedback values Sx'. In one embodiment, the color map selector 70 comprises a slider control 73 for changing a position of colors Sc' on the color map representation C1. In one embodiment, the slider control 73 comprises a displaceable soft button on a touch sensitive display.

In one embodiment, a color value Sc on the color map Cx is associated with a color output of the light source 52. In one embodiment, a position on the color map is associated with a feedback value Sx calculated by the data processor 30. In one embodiment, all one or more light sources 52 on the feedback device 50 are configured to provide a single combined color impression corresponding to the color value Sc selected from the color map Cx based on the feedback value Sx. In one embodiment, the light source 52 comprises one or more colored LEDs. In one embodiment, the feedback device 50 is configured to provide real-time feedback to a user, i.e. feedback is provided while exercising. For example, the feedback device is worn on the body at a position that the light source can be easily viewed while exercising, in particular running, to provide visual feedback.

While shown as separate entities in these and other figures, some components, structures, or functional blocks can be partially or fully integrated or even be formed by the same device. For example, the data processor 30 and/or color mapper 40 can be integrated in any of the readout device 20, feedback device 50, mode selector 60 and/or color map selector 70. The data processor 30 and/or the color mapper 40 can be embodied in hardware and/or software that can run on one or more of the devices. One or more components of the present system can be provided by running suitable software on a generic or special purpose device, e.g. mobile phone or other touch sensitive. In one embodiment, the mode selector 60 and the color map selector 70 are integrated in a single device, e.g. wherein a user interface 72 of the color map selector 70 is displayed on a device after a selection is made in a user interface 62 of the mode selector 60.

Figure 2A:
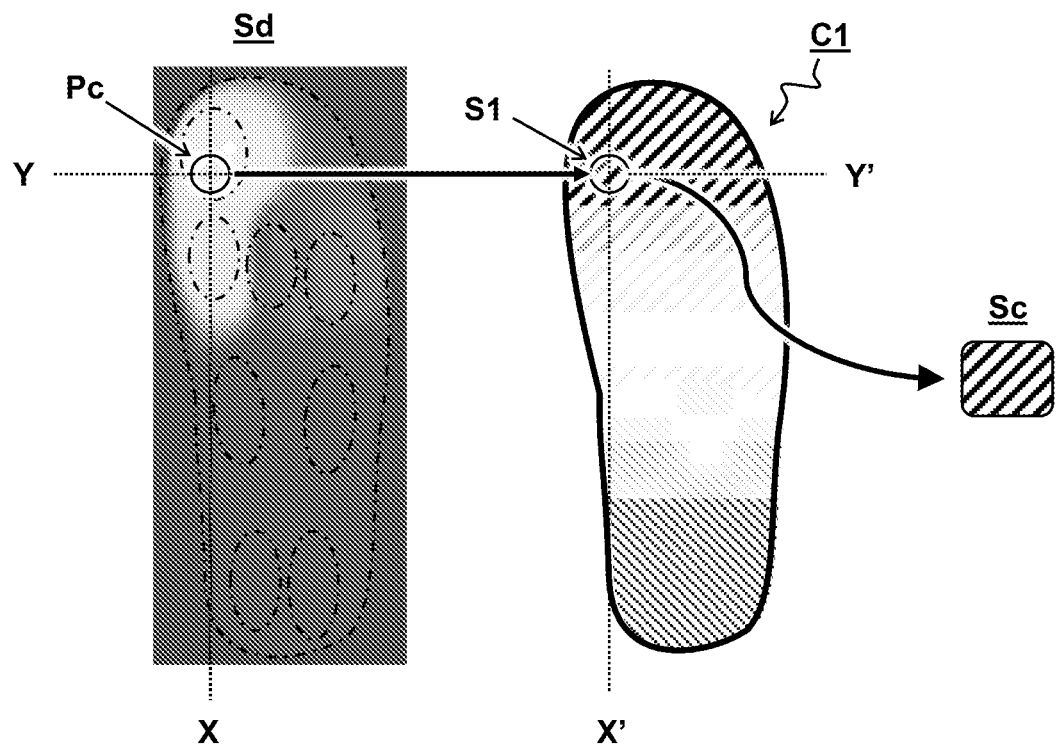
FIG. 2A illustrates an embodiment of a feedback mode.

FIG. 2A shows an embodiment of a feedback mode. The embodiment shows how a feedback value S1 can be calculated from sensor data Sd and mapped onto a color map representation C1 to yield a color value Sc.

In one embodiment, the color map representation C1 comprises a surface profile picture of the pressure sensitive surface. In this way positions X',Y' in the surface profile picture correspond to positions X,Y on the pressure sensitive surface 10. In another or further embodiment, the feedback value S1 comprises a location X,Y on the pressure sensitive surface 10, wherein the location X,Y is mapped onto a corresponding coordinate X',Y' of the surface profile picture for determining the color value Sc. In another or further embodiment, the feedback value S1 comprises a coordinate X,Y of a center of pressure Pc on the pressure sensitive surface 10 calculated from the sensor data Sd, wherein the coordinate X,Y of the center of pressure Pc is mapped onto a corresponding coordinate X',Y' of the surface profile picture for determining the color value Sc. In one embodiment, the feedback value S1 comprises a strike index consisting of coordinate Y of a center of pressure along a length direction of the foot measured at initial impact of the foot.

One algorithm can e.g. be as follows. Detect a step (=foot landing on sufficiently hard surface resulting in a pressure increase on the insole) by continuously sensing the pressure data from the insole and compare it with a threshold. A step is detected if the threshold is exceeded. Upon step detection, measure and store pressure data from n sensors as "Pn". Calculate center of pressure on local electronics using known sensor location (Xn, Yn). A center of pressure can e.g. be calculated from $$Y_c = \frac{\sum_{m=2}^{n}(P_m \cdot Y_m)}{\sum P_n}$$

$$X_c = \frac{\sum_{m=2}^{n}(P_m \cdot X_m)}{\sum P_n}$$

In one embodiment, center of pressure data is sent wirelessly to a mobile phone. The phone performs moving average algorithm(s) to provide noise immunity and a smooth graphical experience. Several options are available to calculate strike index: If only one insole is detected, only the strike index from that insole is calculated. In combined insole mode, that is when two insoles with pressure sensors have been detected and the user is only interested in a single strike index representation, the strike index from the left foot is averaged with the strike index from the right foot. In dual insole mode, that is when two insoles with pressure sensors have been detected and the user is interested in a separate representation of the left and right foot, the strike index is calculated for the left foot and the right foot—resulting in two strike index figures. Also other embodiments and modes are possible. In one embodiment a center coordinate is displayed along a length of the foot: Yc at each landing of the foot. In one embodiment, a color map comprises a profile picture of the pressure sensitive surface (insole) with gradient color scale along the length of the foot.

In one embodiment, feedback may comprise a color that indicates where along the length a person first lands (fore foot/back foot). Further feedback may be provided by a horizontal bar on screen for average foot landing zone (=strike index). User settable and adaptable graphical indicators on a user interface may identify good and bad zones for foot landing location/strike index.

One method comprises receiving sensor data Sd corresponding to a pressure distribution on a pressure sensitive surface 10; processing the sensor data Sd according to a feedback algorithm Ax to calculate a feedback value Sx comprising a coordinate X,Y on the pressure sensitive surface 10; mapping the coordinate X,Y on the pressure sensitive surface 10 onto a coordinate X',Y' of a color map Cx to determine a color value Sc; controlling a light source 52 on a user wearable device to emit a color based on the color value. Preferably, the color map is configurable by a user interface 72 comprising a representation of a surface profile of the pressure sensitive surface 10, wherein the surface profile is filled with color values according the coordinates of the color map.

Figure 2B:
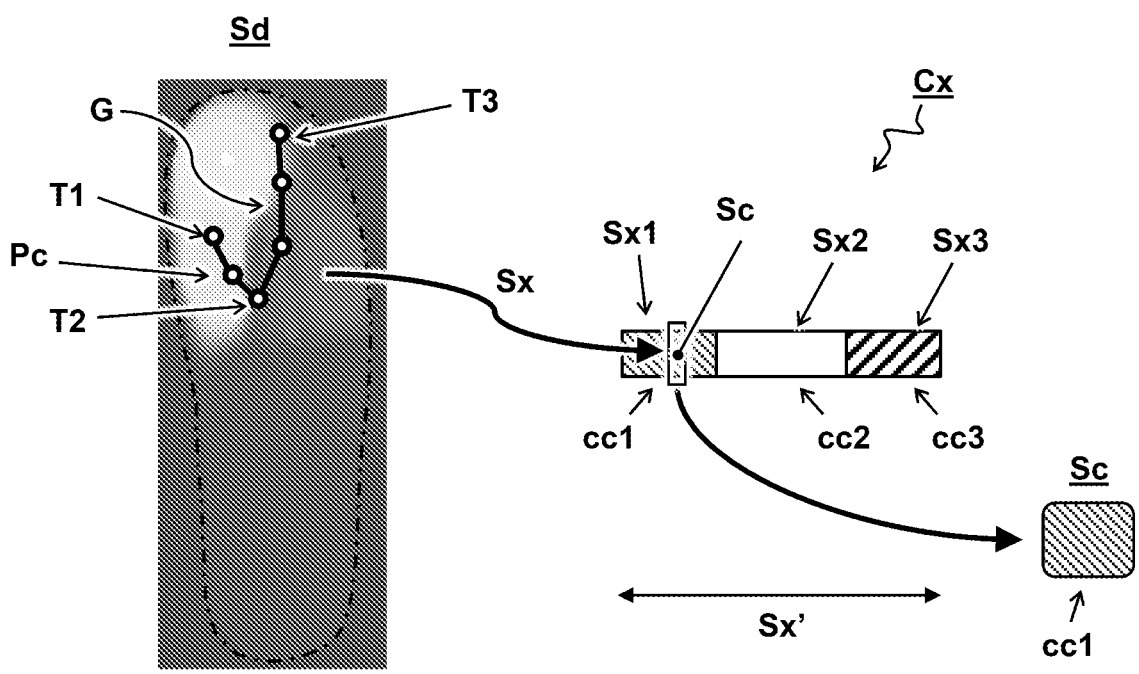
FIG. 2B illustrates another embodiment of a feedback mode.

FIG. 2B illustrates another embodiment of a feedback mode. The embodiment shows how a feedback value Sx can be calculated from sensor data Sd and mapped onto a color map Cx to yield a color value Sc.

In one embodiment, the feedback value Sx is a single number. In one embodiment, the color map Cx comprises a color scale defining color values Sc over a range of feedback values Sx'. In one embodiment, a color value Sc' of the color map Cx is defined as a function of feedback value Sx'. In one embodiment, the color map Cx comprises color values defining a hue of light output Sf from the light source. In one embodiment, the color map Cx defines a first color cc1 on one end of the range Sx' at a relatively low feedback value Sx1 and a second color cc3 on another end of the range Sx' at a relatively high feedback value Sx3; wherein the first and second colors cc1,cc3 have a contrasting hue. In one embodiment, the color map Cx comprises color values defining a brightness of light output Sf from the light source.

In one embodiment, the color map Cx comprises at least two distinct colors, i.e. colors with different hue. In one embodiment, the color map Cx comprises at least three distinct colors cc1,cc2,cc3. In one embodiment, the color map comprises a gradient color scale. In one embodiment, the color map is defined by a gradient color transition between three or more colors. In one embodiment, the color map Cx comprises a color scale of color values Sc as a function feedback values Sx wherein a second color cc2 is between a first color cc1 and a third color cc3, wherein the first color cc1 and third color cc3 are distinctly contrasting colors and the second color cc2 is a neutral color such as white. While colors are represented here by grayscale and/or patterned filling, in reality these can be other colors which can not be displayed in a black and white document.

Color is a visual perceptual property that may depend on a spectral distribution (wavelength and intensity) of light and a perceived interaction of this light with receptors in the (human) eye. Colors may vary in different ways, including hue (e.g. red, green, blue), saturation, and brightness. By defining a color space, colors can be identified numerically by their coordinates. Alternatively, or in addition, colors can be represented by relative contributions of spectral components, e.g. RGB. A light source for the feedback device may similarly employ multiple colored lights whose combined contribution provides the feedback color.

Visible contrast also simply referred to as 'contrast', is the perceived distinction between color, e.g. perceived by an average human. When visible contrast is increased between colors, the colors can be better told apart. Complementary colors, e.g. from a color wheel, may represent high chromatic contrast. In one definition, two colors are called complementary if, when mixed in the proper proportion, they produce a neutral color (grey, white, or black). Examples of complementary colors pairs may include: green-red, purple-yellow, and blue-orange. Also different colors that are not complementary may provide sufficient contrast, e.g. red-yellow. Besides chromatic contrast, there may also be achromatic contrast, depending on the relative intensity, i.e. lightness of the image parts. For example, black-white represent a high level of achromatic contrast. In some cases high contrast may be established by combining complementary coloring and increasing an intensity difference.

Color and contrast may comprise a physiological component as perceived lightness of a color may depend on a sensitivity of the eye to specific colors, e.g. being more sensitive to green light. Color and contrast may also comprise a psychological component. For example, two intense colors may compete for 'attention' in the mind of a user. In such a case, perceived contrast may be enhanced by making one color lighter and the other darker. It is noted that for the present disclosure it is not necessary for achieving a desired effect that the colors are chosen with a maximum contrast, merely sufficient contrast to unambiguously distinguish between different feedback colors by an average user.

In some aspect of the present disclosure, it may be preferable to use colors that do not provide an instinctive user response for good or bad. For example, a red color may be associated with feedback that something is wrong and a green color that something is right. On the other hand, some parameters of an exercise technique, e.g. running style are neither good nor bad, simply a personal preference or style. For example, landing on the forefoot may conserve energy and reduce the biomechanical load in the knee, but may also lead to increased loading in the foot and Achilles tendon, whereas a rear foot landing would reduce these aspects. Accordingly, it is preferable that a user can choose his own colors on the color map, contrasting or otherwise.

In one embodiment, the feedback value Sx is calculated from a time-dependent measurement of the pressure signal Sp. In one embodiment, the feedback value Sx is calculated from a pressure gait line G formed by a moving center of pressure Pc on the pressure sensitive surface 10. For example, the system comprises a clock and a memory (not shown), wherein the readout device 20 is configured to store a time-dependent measurement of the pressure signal Sp in the memory for processing by the data processor 30.

The clock may be any instrument capable of providing an indication of a passing of time. In particular the clock need not keep an absolute measure of time, since only a time difference may be needed for the determination of one or more parameters. The clock need not necessarily conform to any standard timing device, in particular it is not necessary for the clock to provide time in standard units such as seconds, minutes or hours. Any unit used by the clock may suffice as long as it is a linear in time.

The memory may be any suitable type of memory where data are stored, (e.g., RAM, ROM, removable memory, hard drives, memory cards, etc.) or may be a transmission medium or accessible through a network (e.g., a network comprising fiber-optics, the world-wide web, cables, or a wireless channel using time-division multiple access, code-division multiple access, or other radio-frequency channel). Any medium known or developed that can store and/or transmit information suitable for use with a computer system may be used as the computer-readable medium and/or memory. The memory may also store application data as well as other desired data accessible by the controller/processor for configuring it to perform operational acts in accordance with the present systems and methods. Any type of processor may be used such as dedicated or shared one.

Figure 3A:
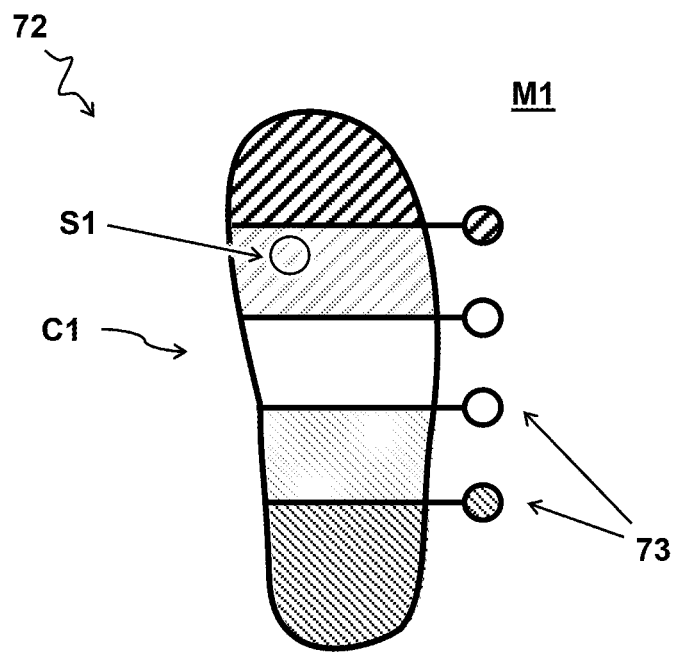
FIGS. 3A through 6B illustrate various user interfaces and color map representations for different feedback modes.

FIG. 3A shows an embodiment of a user interface 72 for displaying a first color map representation C1 map a first feedback mode M1, e.g. wherein a user receives feedback on strike index. Also shown is a location corresponding to a feedback value S1 derived from the pressure data. In the embodiment, the user interface 72 provides slider controls 73 to change a position of the colors relative to the range of feedback values. For example, the present interface can be used to change the color map C1 in the first feedback mode M1.

In one embodiment, an algorithm for calculating strike index comprises one or more of the following steps: receive pressure data from n sensors: Pn; calculate center of pressure (Xc,Yc); output center coordinate along length of foot: Yc at each landing of the foot. A color map may e.g. comprise a profile picture of the pressure sensitive surface (insole) with gradient color scale along the length of the foot. Feedback color may indicate where along the length a person first lands (fore foot/back foot).

Figure 3B:
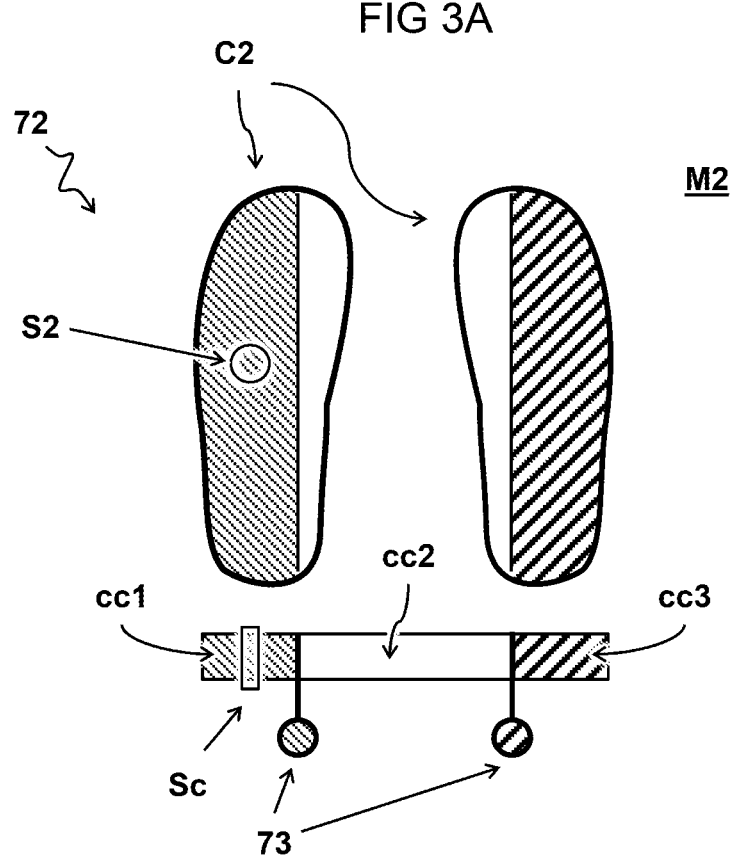

FIG. 3B shows an embodiment of another user interface 72 for displaying a second color map representation C2 in a second feedback mode M2, e.g. wherein a user receives feedback on balance.

In one embodiment, the pressure sensitive surface 10 comprises a first insole and a second insole, placeable in a left and right shoe of a user. In one embodiment, in at least one feedback mode M2, the feedback value S2 is based on a comparison between pressure signals Sp from the first insole and pressure signals Sp from the second insole. In another or further embodiment, the feedback value S2 comprises a balance index consisting of a time difference between a first time duration that pressure is registered on the first insole and a second time duration that pressure is registered on the second insole. In one embodiment, a first color cc1 on the color map C2 is mapped to a balance index wherein the first time duration is larger than the second time duration by a threshold amount of time, and a contrasting second color cc3 on the color map C2 is mapped to a balance index wherein the second time duration is larger than the first time duration by a threshold amount of time wherein a the color map Cx comprises a neutral color cc2 between the thresholds.

In one embodiment, an algorithm for calculating balance comprises one or more of the following steps: receive pressure data (Pl,Pr) from sensors on left foot L and right foot R as function of time; calculate time spent on each foot (Tl,Tr) (with >threshold pressure); output balance fraction of time spent on each foot: (Tl−Tr)/(Tl+Tr) after each liftoff of the foot (or sum all pressure data from both feet, and each individual foot separately, divide the total pressure by each foot to establish a percentage balance between the feet). A color map color map e.g. comprises a gradient color scale from −1 (right foot) to 1 (left foot) wherein 0=fully balanced wherein feedback color indicates tendency to spend more time on left or right foot. Alternative, or in addition to accumulated time per foot, also accumulated pressure per foot can be compared to provide balance feedback.

Figure 4A:
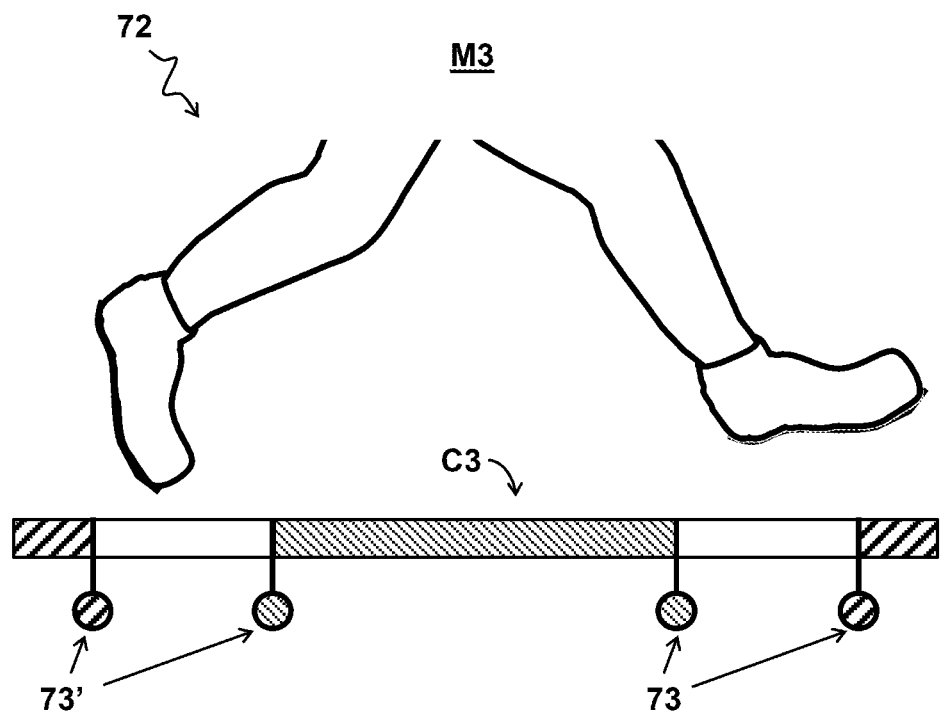

FIG. 4A shows an embodiment of another user interface 72 for displaying a third color map representation C3 in a third feedback mode M3, e.g. wherein a user receives feedback on stride length. For example, in the mode M3, the feedback value S3 is based on a pace frequency calculated from a time between pressure signals Sp from the first insole and pressure signals Sp from the second insole. In another or further embodiment, the feedback value S3 comprises a stride length index based on a runner speed divided by pace frequency wherein the color map C3 defines color values as a function of stride length. In one embodiment, a runner speed is derived from a time resolved measurement of the pressure distribution. In one embodiment, the system comprises a GPS or other location or speed determining device for determining runner speed.

In one embodiment, an algorithm for calculating stride length comprises one or more of the following steps: receive pressure data from sensors to determine number of steps as function of time; receive speed (m/s) as a function of time; calculate stride length (m) as speed (m/s) divided by step frequency (1/s); output stride length after each landing of the foot. The color map may e.g. be gradient color scale from 0 to x meter wherein feedback color indicates stride length (short or long).

In another or further embodiment, an algorithm for calculating stride length comprises one or more of the following steps: Detect a step on local electronics (=foot landing on sufficiently hard surface resulting in a pressure increase on the insole) by continuously sensing the pressure data from the insole and compare it with a threshold. A step is detected if the threshold is exceeded. Start timer upon step detection on local electronics. Detect a foot lift-off on local electronics (=foot rising from sufficiently hard surface resulting in a pressure decrease on the insole) by continuously sensing the pressure data from the insole and compare it with a threshold. A lift-off is detected if the threshold is exceeded. Detect a second step on local electronics (=foot landing on sufficiently hard surface resulting in a pressure increase on the insole) by continuously sensing the pressure data from the insole and compare it with a threshold. A step is detected if the threshold is exceeded. Stop timer upon second step detection on local electronics. Send time difference of timer values on start-stop events wirelessly to phone. Determine number of steps as function of time by calculating the inversion of the step time. receive speed (m/s) as a function of time. calculate stride length (m) as speed (m/s) divided by step frequency (1/s). output stride length after each landing of the foot. A color map may e.g. comprise a gradient color scale from 0 to 2 meter, wherein feedback color indicates stride length (short or long).

In a further embodiment stride length is adjusted to be a function of the horizontal speed of the user. This allows the user to better understand their stride length performance since higher speeds will generally result in longer stride lengths, it is important for the user to understand their relative stride length adjusted for speed, wherein an optimum stride length (not too long and not too short) at the same speed has been shown to be an indication of higher efficiency and lower risk of injury.

Figure 4B:
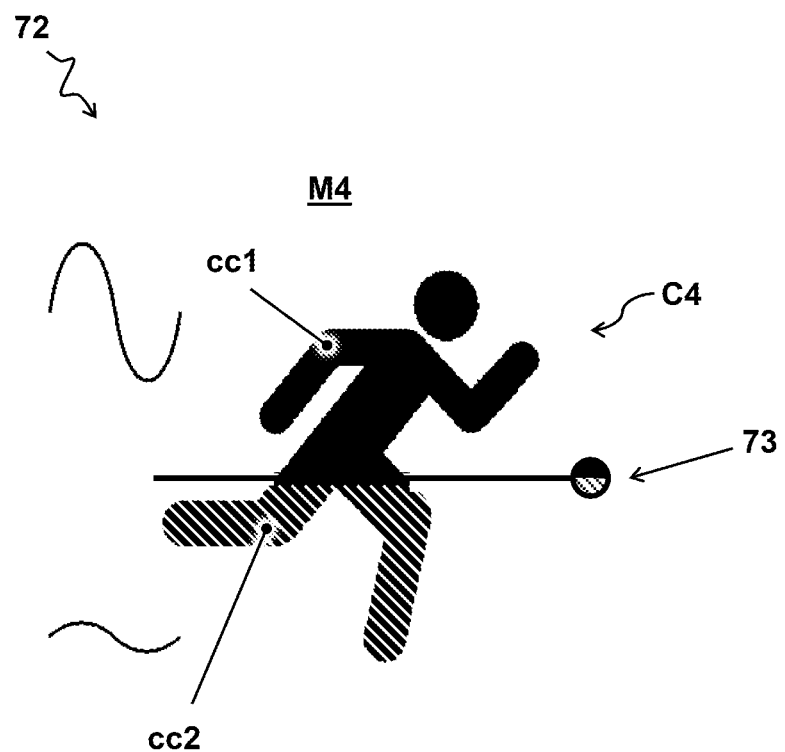

FIG. 4B shows an embodiment of another user interface 72 for displaying a fourth color map representation C4 in a fourth feedback mode M4, e.g. wherein a user receives feedback on vertical oscillation or vertical displacement of the center of mass. For example, in the feedback mode M4, the feedback value S4 is based on a time difference between pressure signals Sp from the first insole and pressure signals Sp from the second insole. In another or further embodiment, the feedback value S4 comprises a vertical oscillation index indicative of a vertical displacement of a runner's center of mass off the ground wherein the color map C4 defines color values as a function of oscillation height.

In one embodiment, an algorithm for calculating vertical displacement of mass comprises one or more of the following steps: receive pressure data from sensors as function of time; calculate air time between either foot touching the ground; output air time after each landing of the foot. Use air time (flight time) to calculate vertical displacement of the center of mass using the equation s=ut+½ at ˆ2 where s=vertical displacement, u=initial velocity (0 in vertical axis), t=time and a=acceleration due to gravity 9.81 m/sˆ2. For example, the color map can be gradient color scale from 0 to x meter (height of oscillation).

In another or further embodiment, an algorithm for calculating vertical oscillation comprises one or more of the following steps: Detect a foot lift-off on local electronics (=foot rising from sufficiently hard surface resulting in a pressure decrease on the insole) by continuously sensing the pressure data from the insole and compare it with a threshold. A lift-off is detected if the threshold is exceeded. Start timer upon lift-off detection on local electronics. Detect a step on local electronics (=foot landing on sufficiently hard surface resulting in a pressure increase on the insole) by continuously sensing the pressure data from the insole and compare it with a threshold. A step is detected if the threshold is exceeded. Stop timer upon step detection on local electronics. Send time difference, t_Air, of timer values on start-stop events wirelessly to phone Calculate the vertical oscillation v_Osc by: $v_{osc}=½·g·(t\_Air/2)^2$. A color map may e.g. comprise a gradient color scale from 0 to 0.5 meter wherein feedback color indicates oscillation (short or long).

Figure 5A:
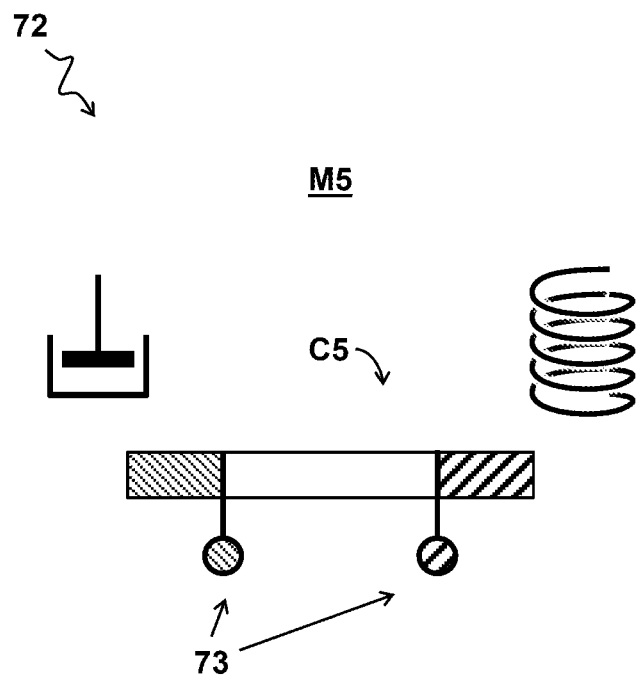

FIG. 5A shows an embodiment of another user interface 72 for displaying a fifth color map representation C5 in a fifth feedback mode M5, e.g. wherein a user receives feedback on reactivity. For example, in the feedback mode M5, the feedback value S5 is based on the timing of a gait line registered by the pressure sensitive surface. In another or further embodiment, the feedback value S5 comprises a reactivity index based on a time difference between a first registered moment that the subject's foot starts touching the ground and a second timestamp T2 at a moment that the center of pressure reaches the most backwards registered position along the gait line with respect to a length of the foot wherein the color map C4 defines color values as a function of reactivity, wherein one end of the color map with a first color corresponds to a spring-like or elastic running style and an opposite end of the color map with a contrasting second color corresponds to a viscous or damped running style.

In one embodiment, an algorithm for calculating reactivity comprises one or more of the following steps: receive pressure data as function of time; calculate for each time frame a center of pressure Py(t) along a length of the foot; calculate the loading time (dT) between the moment the foot first touches the ground (T1) and the moment the center of pressure reaches its most backward position (T2); output reactivity, e.g. R~1/dTˆ2 (heel strike: R=0) after each liftoff of the foot. A color map may e.g. comprise a gradient color scale from 0 to 10 (secondsˆ−2) wherein feedback color indicates reactivity (higher reactivity is shorter loading time is more reactive or spring-like)

Figure 5B:
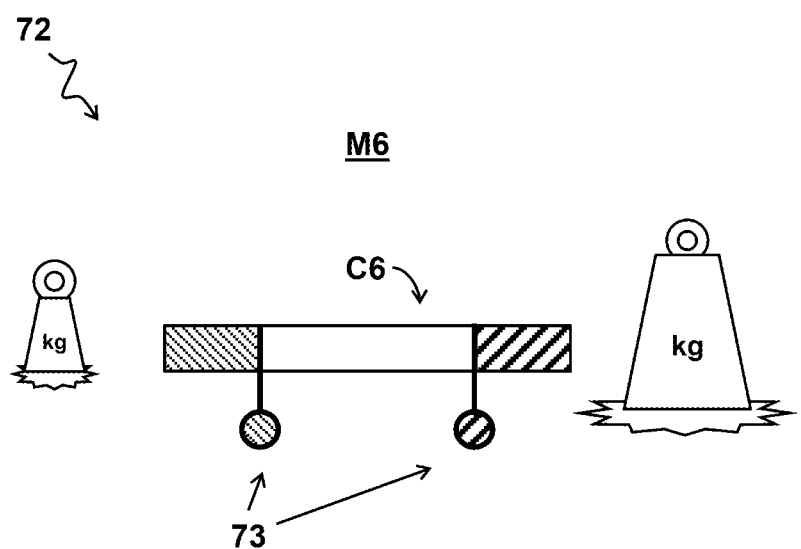

FIG. 5B shows an embodiment of another user interface 72 for displaying a sixth color map representation C6 in a sixth feedback mode M6, e.g. wherein a user receives feedback on reactivity. For example, in the feedback mode M6, the feedback value S6 is based on an integrated pressure signal registered by the pressure sensitive surface 10. In another or further embodiment, the feedback value S6 comprises an impulse index indicative of a peak of integrated pressure signal registered by the pressure sensitive surface 10, wherein the color map C6 defines color values as a function of weight or impulse. In one embodiment, impulse is calculated by an algorithm integrating force over time. Force can e.g. be derived from pressure divided by surface. Feedback colour may e.g. indicate the impulse of the foot (or average impulse of both feet).

Figure 6A:
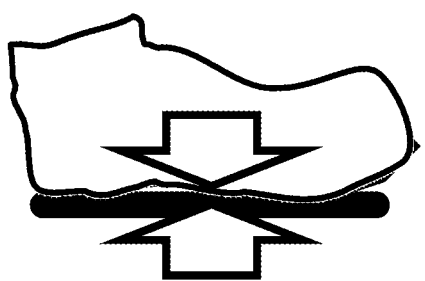
Figure 6A:
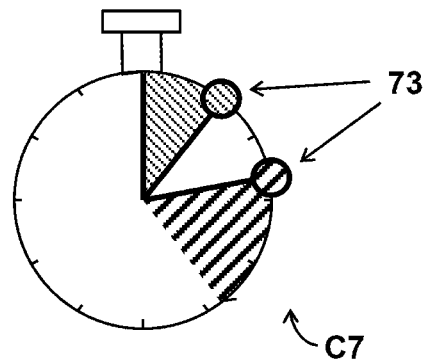

FIG. 6A shows an embodiment of another user interface 72 for displaying a seventh color map representation C7 in a seventh feedback mode M7, e.g. wherein a user receives feedback on contact time. For example, in the feedback mode M7, the feedback value S6 is contact time wherein more than a threshold pressure is exerted on the pressure sensitive surface 10, wherein the color map C6 defines color values as a function of contact time.

In one embodiment, an algorithm for calculating contact time comprises one or more of the following steps: Detect a step on local electronics (=foot landing on sufficiently hard surface resulting in a pressure increase on the insole) by continuously sensing the pressure data from the insole and compare it with a threshold. A step is detected if the threshold is exceeded. Start timer upon step detection on local electronics. Detect a foot lift-off on local electronics (=foot rising from sufficiently hard surface resulting in a pressure decrease on the insole) by continuously sensing the pressure data from the insole and compare it with a threshold. A lift-off is detected if the threshold is exceeded. Stop timer upon lift-off detection on local electronics. Send time difference of timer values on start-stop events wirelessly to phone; output contact time after each liftoff of the foot. A color map may comprise e.g. a gradient color scale from 0 to 1 (seconds), wherein feedback color indicates contact time of the foot on the ground.

In another or further embodiment, contact time is adjusted as a function of the horizontal speed of the user. This allows the user to better understand their contact time performance since higher speeds will generally result in shorter contact times, it is important for the user to understand their relative contact time adjusted for speed, wherein a shorter contact time at the same speed has been shown to be an indication of higher efficiency and lower risk of injury.

Figure 6B:
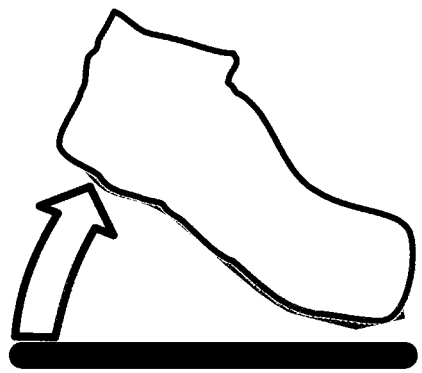
Figure 6B:
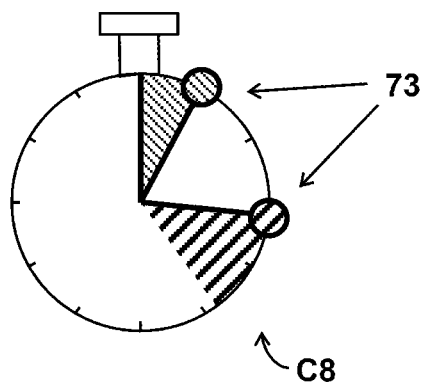

FIG. 6B shows an embodiment of another user interface 72 for displaying an eighth color map representation C8 in an eighth feedback mode M8, e.g. wherein a user receives feedback on heel lift speed. For example, in the feedback mode M8, the feedback value S8 comprises a heel lift speed based on a time difference between a moment T2 that the center of pressure reaches the most backwards registered position along the gait line with respect to a length of the foot and a moment T3 that the foot leaves the ground, wherein the color map C8 defines color values as a function of heel lift speed or time.

Figure 7:
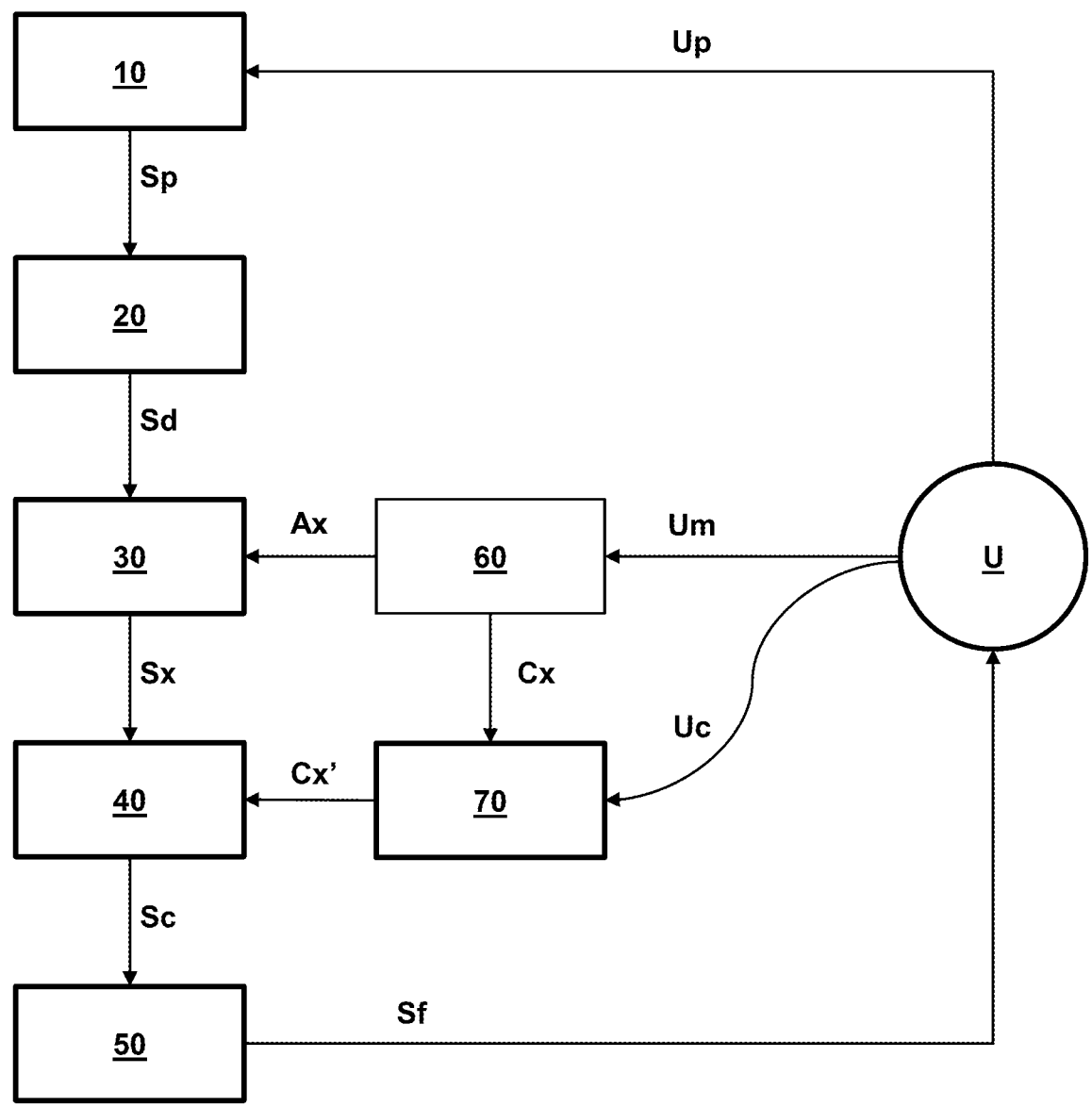
FIG. 7 illustrates a flow diagram of an embodiment of a method for generating feedback on running style.

FIG. 7 illustrates a flow diagram of a method for providing feedback on running style.

The method comprises selecting a feedback mode with a mode-specific feedback algorithm Ax and color map Cx; receiving sensor data Sd corresponding to pressure exerted on a pressure sensitive surface 10 during running; processing the sensor data Sd according to the mode-specific feedback algorithm Ax to calculate a feedback value Sx; mapping the feedback value Sx onto the mode-specific color map Cx to transform the feedback value Sx into a color value Sc; and controlling a light source to generate variable color light output Sf based on the color value Sc;

In one embodiment, the feedback mode M1 is selected from a plurality of feedback modes wherein each feedback mode is distinguished by a mode-specific feedback algorithm Ax and color map Cx. In another or further embodiment, the feedback mode M1 is selectable by user interaction Um with a mode selector 60, wherein the mode selector 60 defines a feedback algorithm Ax and color map Cx based on the user selected feedback mode. While the ability of selecting between different feedback modes is a preferred embodiment, providing benefit to training different aspects of a running style, alternatively, a system or method can also be envisaged providing only a single feedback mode, e.g. selected from the present embodiments or otherwise.

For example, in one embodiment, the feedback algorithm Ax comprises calculation of a pressure coordinate of a location on the pressure sensitive surface 10, wherein the pressure coordinate X,Y is mapped onto a corresponding map coordinate X',Y' of a location on the color map Cx to determine the color value Sc. In another or further embodiment, the pressure coordinate X,Y is calculated from a center of pressure of a pressure distribution exerted on the pressure sensitive surface. In another or further embodiment, the color map Cx defines a color value Sc for each location X,Y on the pressure sensitive surface.

In one embodiment, the sensor data Sd is received from a readout device 20 based on pressure signals Sp from the pressure sensitive surface 10. In one embodiment, the sensor data Sd is processed by a data processor 30. In one embodiment, the feedback value Sx is mapped on a color value Sc by a color mapper 40, wherein the color mapper maps the color value by a table lookup and/or interpolation of color values defined at specific feedback values. In one embodiment, a color value and/or position colors on the color map Cx as a function of feedback value Sx are defined by a color map selector 70. In one embodiment, the color map selector 70 is operable to receive user input Uc to change a color value and/or position.

It will be appreciated that user "U" can interact with and receive feedback from the system in various ways, e.g. by the pressure Up he exerts on the pressure sensitive surface 10, by the interaction Um, Uc with the mode selector 60 and/or color map selector 70, and by the feedback signal received from the feedback device 50.

FIGS. 8A-8D show screenshot images of an embodiment of a computer program ("App") running on a mobile device, e.g. telephone. Accordingly methods, or parts thereof, as describe herein can be stored on a computer readable medium with program instructions, wherein the program instructions, when executed on one or more computers, cause the one or more computers to execute the respective method.

Figure 8A:
FIGS. 8A-8D show screenshot images of an embodiment of a computer program ("App") running on a mobile device.

FIG. 8A shows a selection menu wherein the user can select categories for feedback. Besides feedback on running style, feedback can also be provided for hiking, sprinting, walking, etcetera. Also other exercise aspects can be monitored. In a further menu (not shown), the user can make a selection of a particular feedback parameter, e.g. strike index, balance, stride length, etcetera.

Figure 8B:
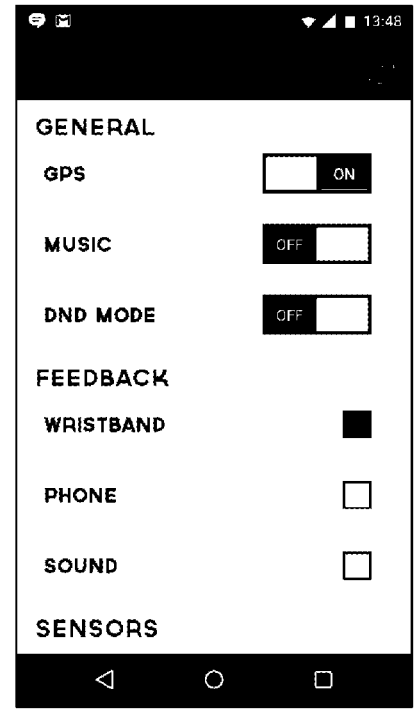

FIG. 8B shows a settings menu that enables a user to select e.g. equipment and feedback. For example, it can be selected whether the user wants feedback via a wristband device and/or the phone and/or sound. In one embodiment, color feedback is provided by the phone display itself, e.g. worn on the shoulder or wrist. Preferably though, a separate wrist device is used that can be relatively light weight and easily viewed while running.

Figure 8C:
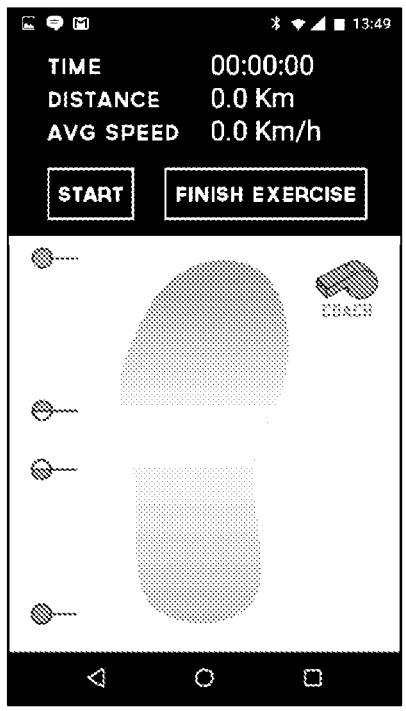

FIG. 8C shows a color map selector menu for the first feedback mode (M1, strike index) with slider bars to adjust a position of the color ranges. Also other buttons, information, and functionality can be present.

Figure 8D:
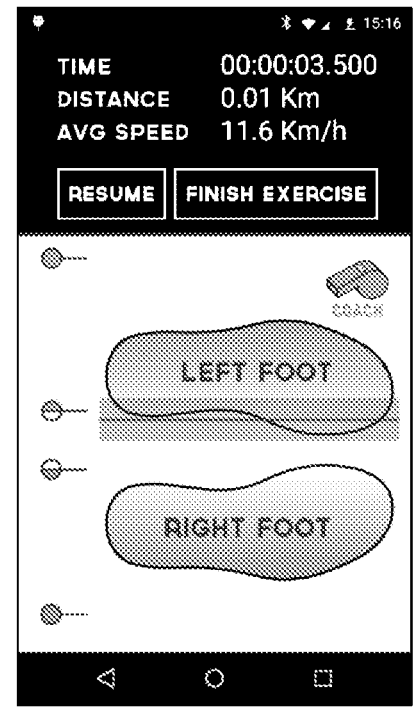

FIG. 8D shows a color map selector menu for the second feedback mode (M2, balance) with slider bars to adjust a position of the color ranges. The interface also shows a location of a previously or currently measured balance position.

Figure 9A:
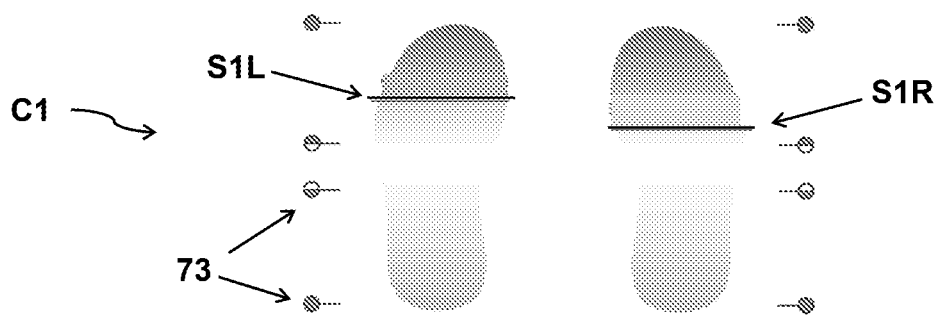
FIGS. 9A-9C illustrate further embodiments of user interfaces and color map representations for different feedback modes.
Figure 9B:
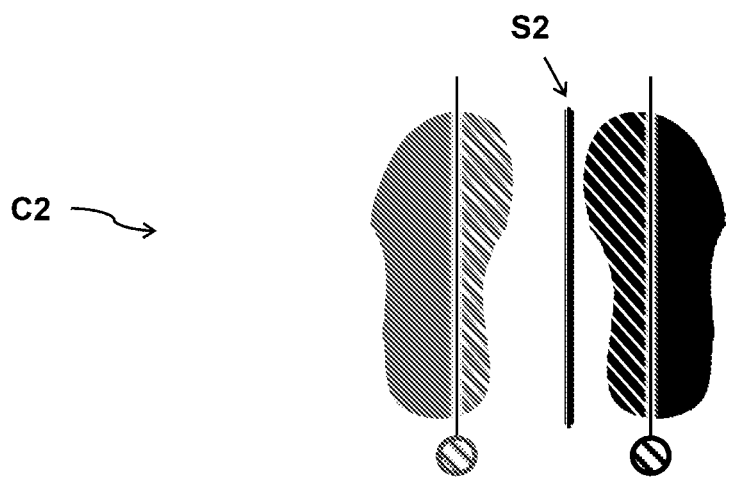
Figure 9C:
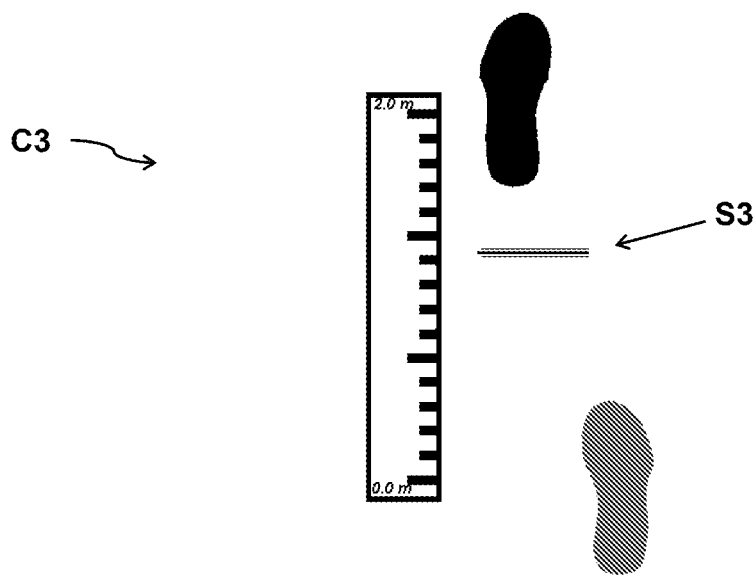

FIG. 9 show embodiments of color map representations C1,C2,C3 for different feedback modes. FIG. 9A corresponds to strike index feedback for both feet separately. FIG. 9B corresponds to balance feedback FIG. 9C corresponds to stride length. In one embodiment, e.g. as illustrated in these figures, the color map selector is configured to display a location of one or more feedback values S1L/S1R,S2,S3 on a respective color map representation C1,C2,C3. This can allow the user to inspect e.g. after an exercise what is the position of a past or current feedback value relative to the color map representation and adjust the color ranges accordingly.

For the purpose of clarity and a concise description, features are described herein as part of the same or separate embodiments, however, it will be appreciated that the scope of the invention may include embodiments having combinations of all or some of the features described. For example, while embodiments were shown for various different aspects of running or walking style, also alternative ways may be envisaged by those skilled in the art having the benefit of the present disclosure for achieving a similar function and result, e.g. providing feedback on various aspects of exercise or movement technique. For example, systems, components, or program functionality may be combined or split up into one or more alternative components. The various elements of the embodiments as discussed and shown offer certain advantages, such as intuitive feedback on running style. Of course, it is to be appreciated that any one of the above embodiments or processes may be combined with one or more other embodiments or processes to provide even further improvements in finding and matching designs and advantages. It is appreciated that this disclosure offers particular advantages to running and exercise, and in general can be applied for any application wherein feedback on movement is desired, e.g. not only running, but also normal walking, hiking, climbing etcetera.

While the present systems and methods have been described in particular detail with reference to specific exemplary embodiments thereof, it should also be appreciated that numerous modifications and alternative embodiments may be devised by those having ordinary skill in the art without departing from the scope of the present disclosure. For example, embodiments wherein devices or systems are disclosed to be arranged and/or constructed for performing a specified method or function inherently disclose the method or function as such and/or in combination with other disclosed embodiments of methods or systems. Furthermore, embodiments of methods are considered to inherently disclose their implementation in respective hardware, where possible, in combination with other disclosed embodiments of methods or systems. Furthermore, methods that can be embodied as program instructions, e.g. on a non-transient computer-readable storage medium, are considered inherently disclosed as such embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. A system for generating feedback on exercise technique, the system comprising:
   a sensor configured to generate a sensor signal as a function of one or more biomechanical aspects of the exercise technique;
   a readout device configured to generate sensor data based on the sensor signal;
   a data processor configured to process the sensor data to calculate a feedback value;
   a color mapper configured to map the feedback value onto a color map to transform the feedback value into a color value;
   a color map selector configured to provide user customization of the color map, wherein the customization comprises adjustment of one or more of color values and positions on the color map; and
   a wearable feedback device comprising a light source configured to generate a variable color light output based on the color value,
   wherein an intensity and position of the light source is configured to enable an exercising user wearing the wearable feedback device to be able to receive visual feedback in their peripheral vision whilst looking ahead, for enabling the user to perceive direction, obstacles and potential hazards, whilst maintaining a running form.

2. The system according to claim 1, comprising a mode selector configured to provide selection between a plurality of feedback modes,
   wherein the selection of a feedback mode results in selection of a feedback algorithm for the data processor and selection of a color map for the color mapper;
   wherein the selected feedback algorithm and color map are uniquely specific for each feedback mode;
   wherein, based on the selected feedback mode, the data processor is configured to process the sensor data according to the mode-specific feedback algorithm to calculate the feedback value according to the selected feedback mode; and the color mapper is configured to map the calculated feedback value onto the mode-specific color map for transforming the feedback value into the color value according to the selected feedback mode.

3. The system according to claim 2, wherein the mode selector comprises a user input device configured to provide user selection between the plurality of feedback modes.

4. The system according to claim 1, wherein the feedback value is a single number; wherein the color map comprises a color scale defining color values over a range of feedback values; wherein a color value of the color map is defined as a function of feedback value; wherein the color map comprises color values defining a hue of light output from the light source; wherein the color map defines a first color on one end of the range at a relatively low feedback value and a second color on another end of the range at a relatively high feedback value; and wherein the first and second colors have a contrasting hue.

5. The system according to claim 1, wherein the color map selector comprises a user interface depicting a color map representation, wherein the representation comprises a color scale displaying color values over a range of feedback values.

6. The system according to claim 1, wherein the color map selector comprises a slider control for changing a position of colors on the color map representation.

7. The system according to claim 1, wherein the color map selector is configured to display a location of one or more feedback values on a respective color map representation.

8. The system according to claim 1, wherein the color map is defined by a gradient color transition between three or more colors.

9. The system according to claim 1, wherein the system is configured for generating feedback on running or walking style, wherein:
   the sensor comprises a pressure sensitive surface configured to generate a pressure signal as a function of pressure exerted on the pressure sensitive surface during running or walking; and
   a readout device is configured to generate sensor data based on the pressure signal.

10. The system according to claim 9, wherein in at least one feedback mode, the color map representation on the color map selector comprises a surface profile picture of the pressure sensitive surface wherein positions in the surface profile picture correspond to positions on the pressure sensitive surface.

11. The system according to claim 9, wherein in at least one feedback mode, the feedback value comprises a location on the pressure sensitive surface, wherein the location is mapped onto a corresponding coordinate of the surface profile picture for determining the color value.

12. A method for providing feedback on exercise technique, the method comprising:
   selecting a feedback mode with a mode-specific feedback algorithm and color map;
   receiving sensor data corresponding to one or more biomechanical aspects of the exercise technique;
   processing the sensor data according to the mode-specific feedback algorithm to calculate a feedback value, wherein the feedback algorithm comprises calculation of a pressure coordinate of a location on a pressure sensitive surface or determining acceleration of a user's foot;
   mapping the feedback value onto the mode-specific color map to transform the feedback value into a color value, wherein the pressure or acceleration is mapped onto a corresponding map coordinate of a location on the color map to determine the color value; and
   controlling a light source on a wearable feedback device to generate variable color light output based on the color value,
   wherein an intensity and position of the light source is configured to enable an exercising user wearing the wearable feedback device to be able to receive visual feedback in their peripheral vision whilst looking ahead, for enabling the user to perceive direction, obstacles and potential hazards, whilst maintaining a running form.

13. The method according to claim 12, wherein the feedback mode is selected from a plurality of feedback modes, wherein each feedback mode is distinguished by a mode-specific feedback algorithm and color map.

14. A non-transitory computer readable medium with program instructions that when executed on one or more computers, cause the one or more computers to execute a method comprising:
- selecting a feedback mode with a mode-specific feedback algorithm and color map;
- receiving sensor data corresponding to one or more biomechanical aspects of the exercise technique;
- processing the sensor data according to the mode-specific feedback algorithm to calculate a feedback value, wherein the feedback algorithm comprises calculation of a pressure coordinate of a location on a pressure sensitive surface or determining acceleration of a user's foot;
- mapping the feedback value onto the mode-specific color map to transform the feedback value into a color value, wherein the pressure or acceleration is mapped onto a corresponding map coordinate of a location on the color map to determine the color value; and
- controlling a light source on a wearable feedback device to generate variable color light output based on the color value,
- wherein an intensity and position of the light source is configured to enable an exercising user wearing the wearable feedback device to be able to receive visual feedback in their peripheral vision whilst looking ahead, for enabling the user to perceive direction, obstacles and potential hazards, whilst maintaining a running form.

* * * * *